(12) United States Patent
Hausen et al.

(10) Patent No.: US 7,291,157 B1
(45) Date of Patent: Nov. 6, 2007

(54) ANASTOMOSIS TOOL WITH IMPROVED GRAFT LOADING

(75) Inventors: Bernard A. Hausen, Menlo Park, CA (US); Luke W. Clauson, Redwood Shores, CA (US); David L. Bombard, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 0 days.

(21) Appl. No.: 11/451,222

(22) Filed: Jun. 12, 2006

(51) Int. Cl.
*A61B 17/10* (2006.01)
*A61B 17/04* (2006.01)
*A61B 17/08* (2006.01)

(52) U.S. Cl. .................... 606/139; 606/153; 227/175.1
(58) Field of Classification Search ................. 606/232, 606/224, 253, 222; 623/1.23
See application file for complete search history.

(56) References Cited

U.S. PATENT DOCUMENTS

| | | | |
|---|---|---|---|
| 5,067,959 A | | 11/1991 | Korthoff |
| 5,102,418 A | | 4/1992 | Granger et al. |
| 5,474,572 A | * | 12/1995 | Hayhurst ..................... 606/232 |
| 5,972,024 A | | 10/1999 | Northrup, III et al. |
| 6,015,427 A | * | 1/2000 | Mueller et al. ............. 606/232 |
| 6,607,541 B1 | * | 8/2003 | Gardiner et al. ............ 606/151 |
| 6,942,675 B1 | * | 9/2005 | Vargas ........................ 606/153 |

* cited by examiner

*Primary Examiner*—Michael J. Hayes
*Assistant Examiner*—Christina Gettman
(74) *Attorney, Agent, or Firm*—Brian A. Schar (57) ABSTRACT

A surgical tool for performing anastomosis may include a staple holder; a clip detachably connected to the staple holder; a length of suture, wherein a portion of the length of suture is held securely between the clip and the staple holder; and a needle connected to the suture. An incision may be made at one end of the graft vessel to form a flap. The needle may penetrate the wall of the graft vessel proximal to the incision, and the graft vessel may then be parachuted down the suture toward engagement with the clip. In this way, graft loading onto the clip is facilitated.

18 Claims, 10 Drawing Sheets

ANASTOMOSIS TOOL WITH IMPROVED GRAFT LOADING

FIELD OF THE INVENTION

The invention relates to a surgical apparatus and method for performing anastomosis, and more specifically to an improved method of loading a graft vessel onto the surgical apparatus.

BACKGROUND

Anastomosis is a procedure by which two hollow tissue structures are joined together. More particularly, vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

Anastomosis tools and anastomosis devices have been developed to simplify the CABG procedure and improve the quality of patient care. For example, Cardica's C-PORT® distal anastomosis tool allows surgeons to quickly create a high-quality connection between a graft vessel and a coronary artery. A graft vessel is loaded onto the distal end of that tool, and an end of that graft vessel is then connected to the coronary artery by stapling.

BRIEF DESCRIPTION OF THE DRAWINGS

The use of the same reference symbols in different figures indicates similar or identical items.

DETAILED DESCRIPTION

Figure 1:
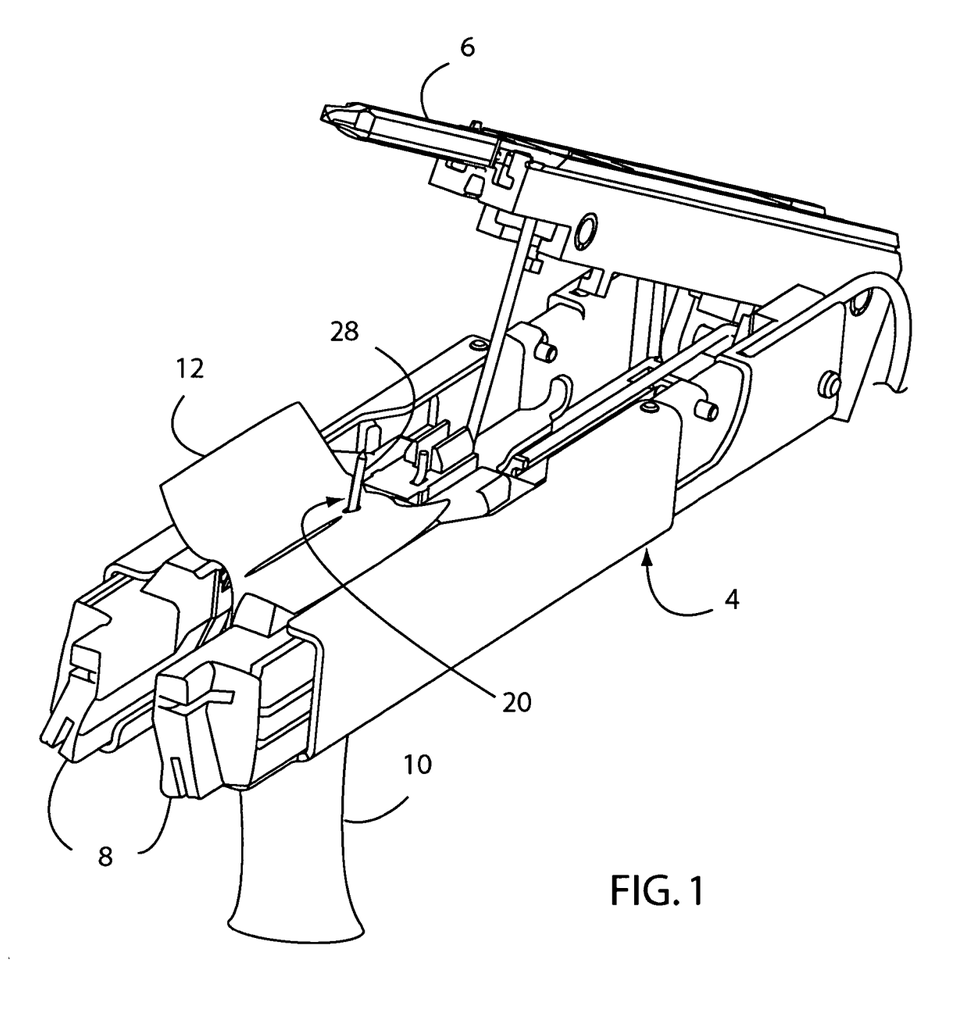
FIG. 1 is a perspective view of the distal end of an anastomosis tool having a staple holder and an anvil.

Referring to FIG. 1, an anastomosis tool 2 may include a staple holder 4 movably connected to an anvil 6, such as disclosed in U.S. patent application Ser. No. 11/054,265, filed on Feb. 9, 2005, which is hereby incorporated by reference in its entirety. The staple holder 4 may include two spaced-apart arms 8 that are substantially parallel to one another. The staple holder 4 may be movable relative to the anvil 6 in any suitable manner, such as by rotation. An exemplary anvil 6 has a height and a width of about 2 mm or less, advantageously about 1 mm or less, and a length of about 2 to 15 mm, advantageously 5 to 12 mm. The length of the anvil will vary depending on the diameter of the graft vessel selected. The length to width ratio of the anvil 6 is substantially between 2:1 and 15:1. A different length to width ratio may be used, if desired. The distal end of the anvil 6 may be sharp or blunt.

Figure 2:
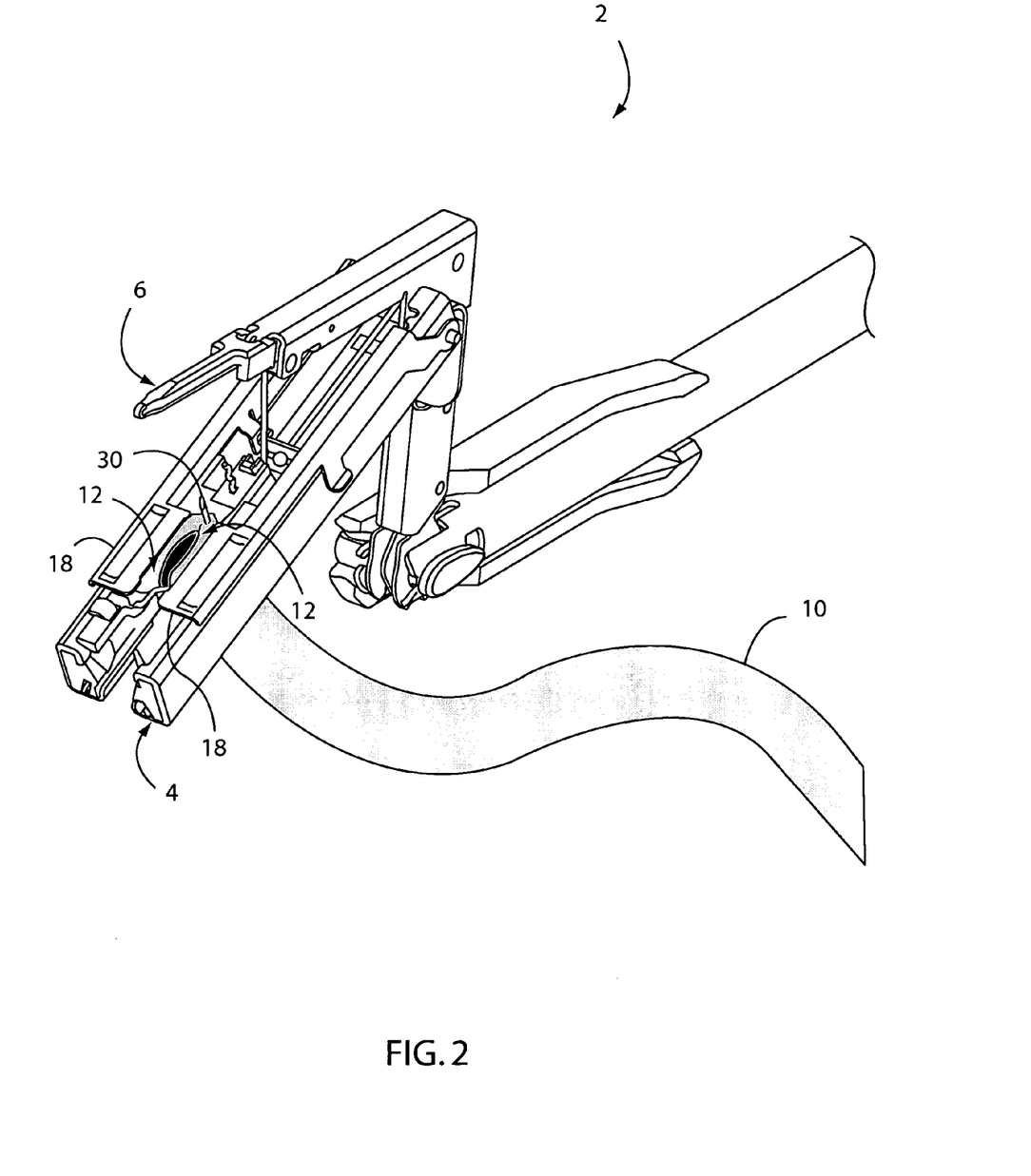
FIG. 2 is a perspective view of the distal end of the anastomosis tool of FIG. 1, holding a graft vessel having a flapped end.
Figure 3:
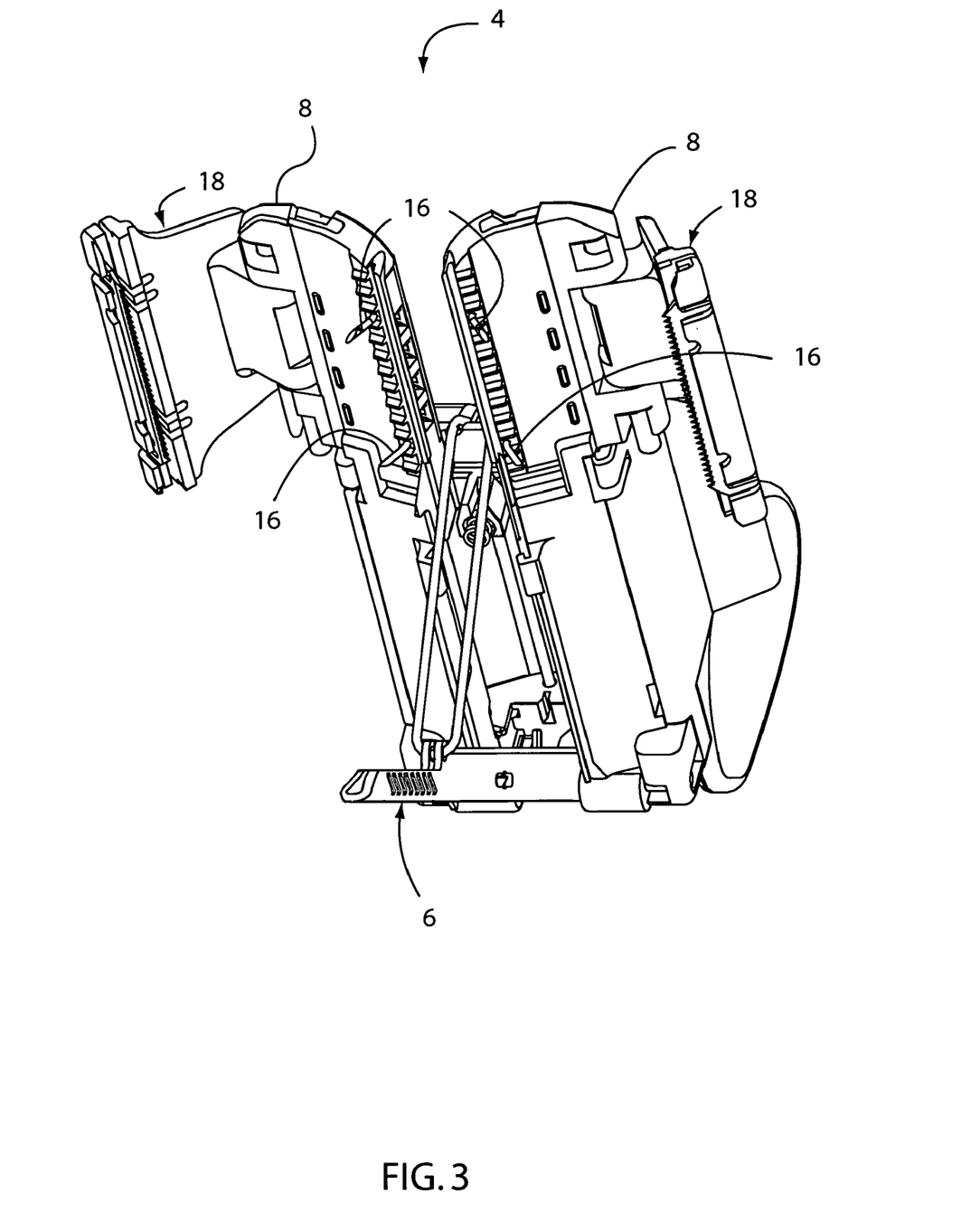
FIG. 3 is a different perspective view of the distal end of the anastomosis tool of FIG. 1.

Referring to FIG. 2, the arms 8 of the staple holder 4 may be spaced apart from one another across at least a part of their length. As a result, a graft vessel 10 can be positioned between the arms 8, such that the arms 8 are positioned on substantially opposite sides of the graft vessel 10. At least one flap 12 is formed at the end of the graft vessel 10, such as disclosed in U.S. patent application Ser. No. 11/054,265. Each arm 8 may be positioned against at least one flap 12, and may hold at least one flap 12 in any suitable manner. Referring also to FIG. 3, one or more spikes 16 optionally may extend outward from at least one of the arms 8. One or more of the spikes 16 penetrate a corresponding flap 12 partially or completely, thereby assisting in holding the flap 12 in place relative to the corresponding arm 8. As an example, at least one arm 8 may include at least one graft clip 18 that exerts force on a corresponding flap 12 to hold that flap securely against the corresponding arm 8.

A graft clip 18 may be connected to each arm 8 in any suitable manner. For example, at least one graft clip 18 may be pivotally connected to the corresponding arm 8 such that it can rotate relative to the corresponding arm 8. Alternately, at least one graft clip 18 is movable relative to the corresponding arm 8 in a different way, such as by sliding. Alternately, at least one graft clip 18 is initially a separate component from the arm 8, and is connectable to the corresponding arm 8. Each graft clip 18 is moveable between an open position and a closed position relative to the corresponding arm 8. In the closed position, the graft clip 18 engages a flap 12 of the graft vessel 10 to hold that flap 12 against the corresponding arm 8 of the staple holder 4. Each graft clip 18 may be locked or otherwise held in the closed position to securely hold a flap 12 between itself and the corresponding arm 8. The graft clip or clips 18 may be configured and operated as disclosed in U.S. patent application Ser. No. 11/054,265.

Figure 4:
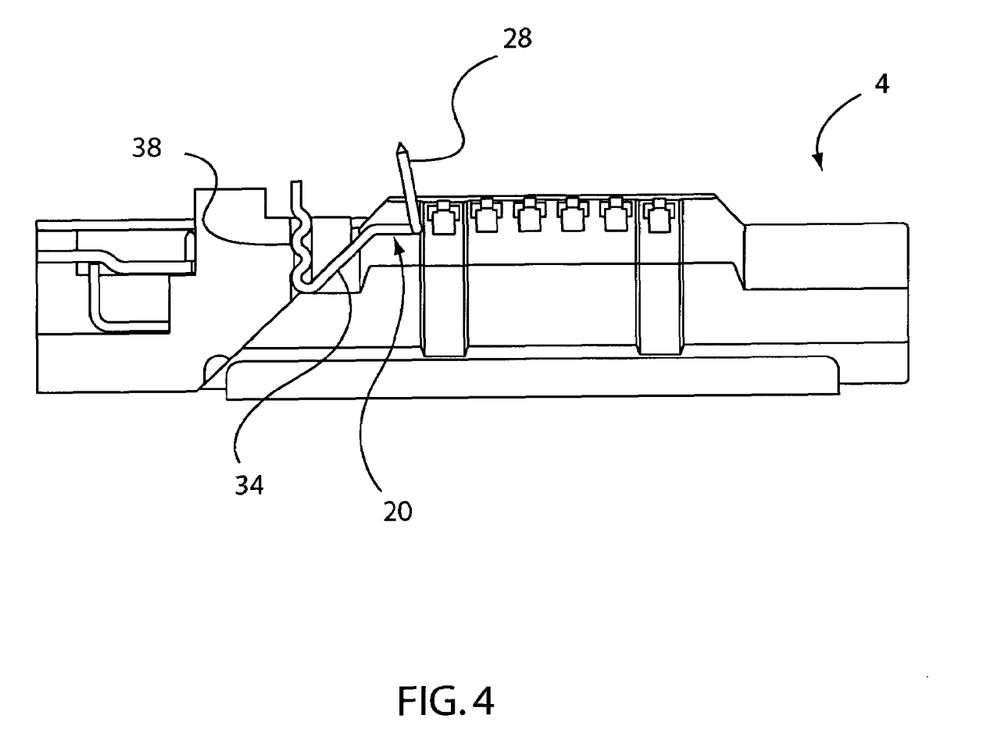
FIG. 4 is a side cross-section view of the staple holder of FIG. 1, showing a graft affixer held by that staple holder.

Referring to FIGS. 1 and 4, a graft affixer 20 is connected to or formed into the staple holder 4. The graft affixer 20 extends outward from the staple holder 4, and may be oriented at least partially toward the anvil 6. The graft affixer 20 penetrates an end of the graft vessel 10 and holds the graft vessel 10 to the staple holder 4, as described in greater detail below. The graft affixer 20 may be any structure or mechanism configured to hold the graft vessel 10 to the staple holder 4. As one example, the graft affixer 20 may be a spike. The tip of the spike may be oriented toward the anvil 6, or in a different direction. As another example, the graft affixer 20 may be a hook. As another example, the graft affixer 20 may be a clip. The graft affixer 20 may include a barb (not shown) at or near its tip, or at a different location, in order to hold the graft vessel 10 more securely.

The graft affixer 20 may be located between the arms 8 of the staple holder 4 near the proximal ends of the arms 8. This proximal position of the graft affixer 20 allows the graft affixer 20 to engage a location on the graft vessel 10 that will be positioned at or near the heel of the anastomosis. Alternately, the graft affixer 20 may be located at any other suitable location relative to the staple holder 4. The graft affixer 20 may be composed of any appropriate material. As one example, the graft affixer 20 may be composed of plastically-deformable material, such as stainless steel. As another example, the graft affixer 20 may be composed at least in part of an elastic or superelastic material, such as nickel-titanium alloy.

Figure 5:
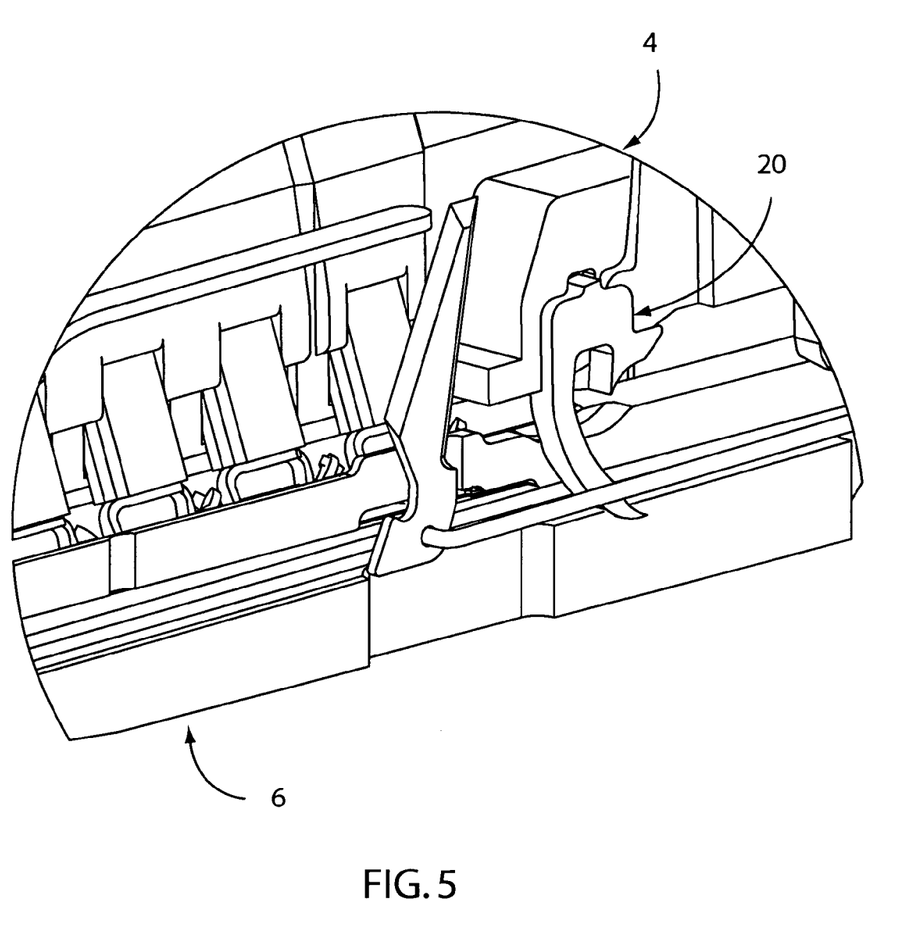
FIG. 5 is a perspective detail view of the staple holder of FIG. 1, showing a graft affixer held by that staple holder.
Figure 6:
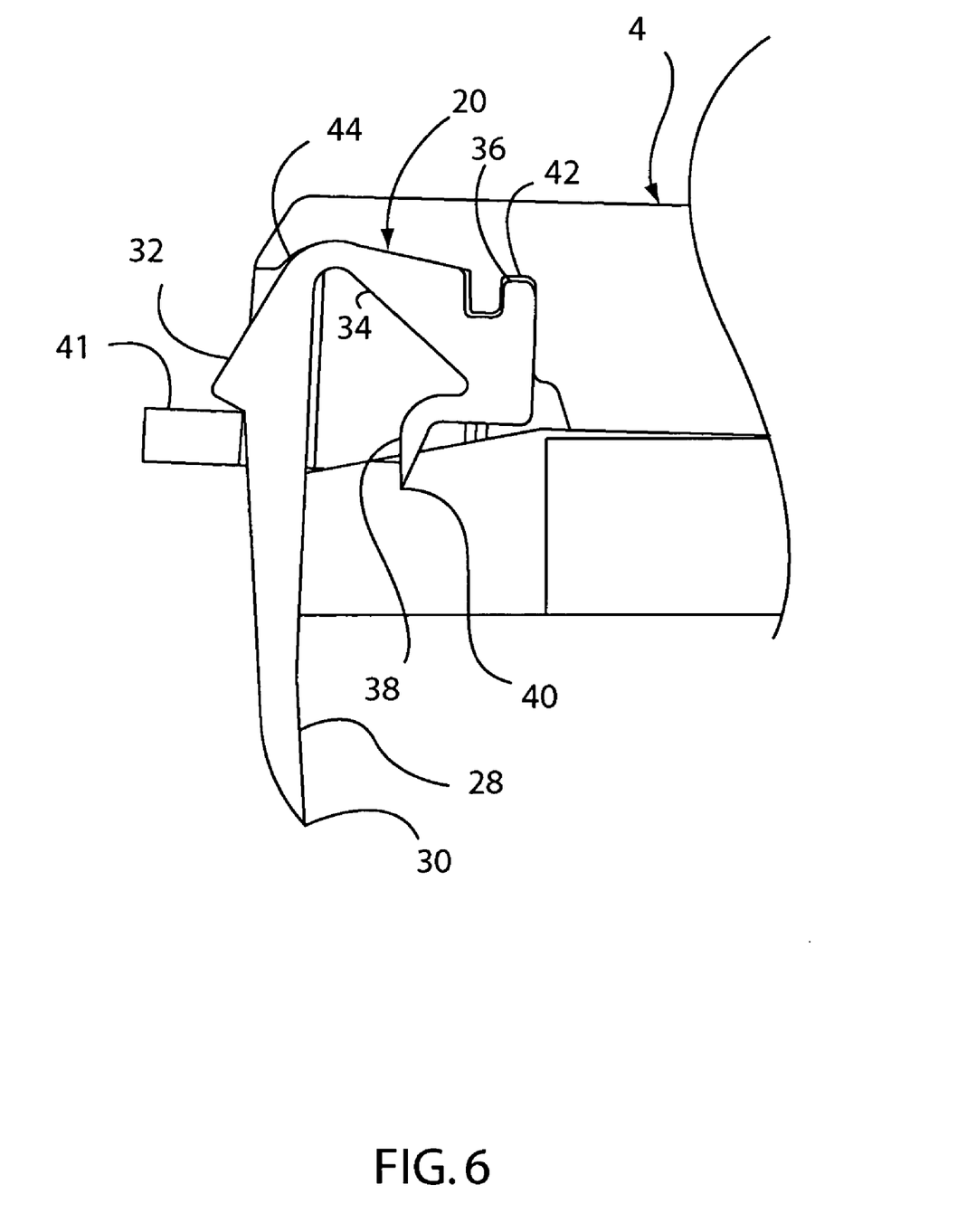
FIG. 6 is a side view of an exemplary graft affixer detachably connected to the staple holder, in an open position.
Figure 7:
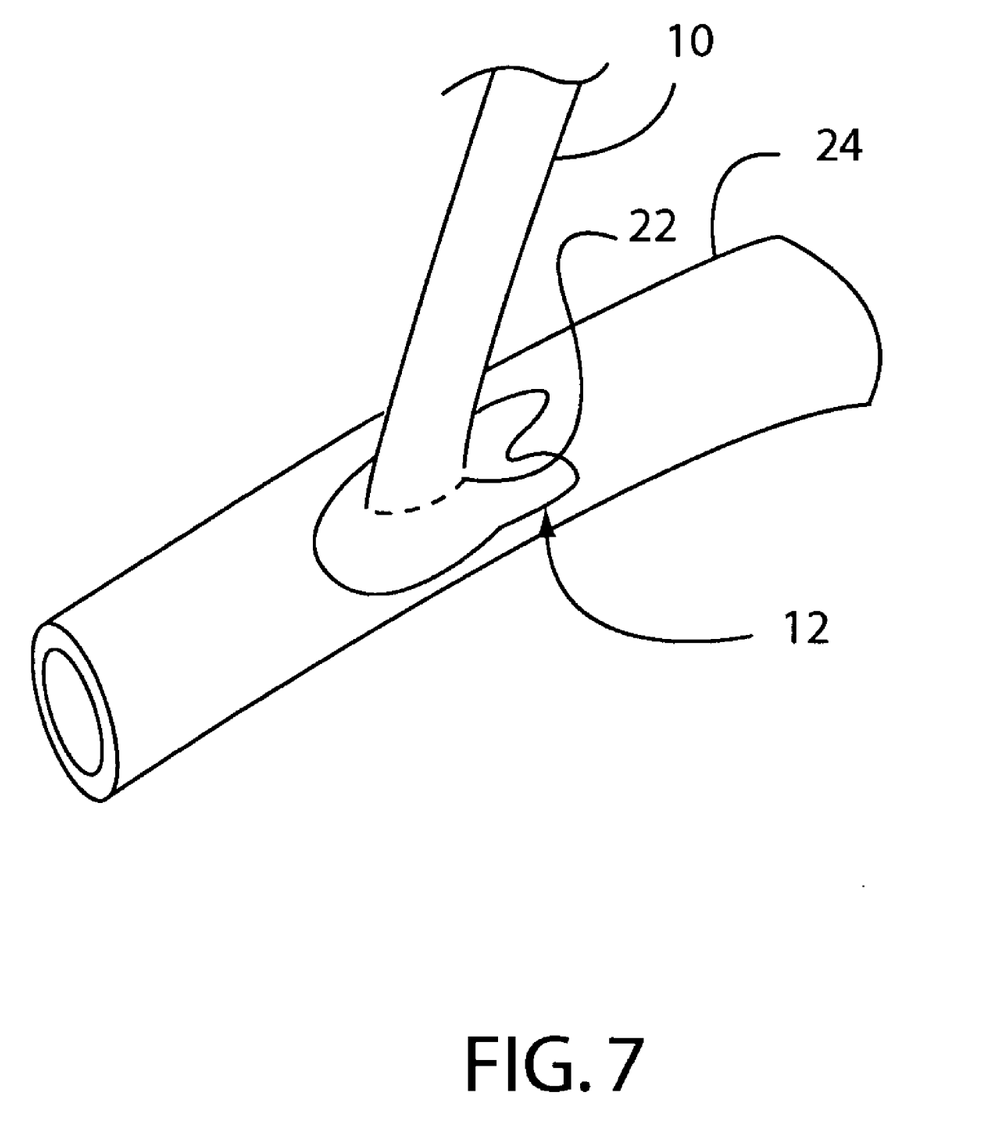
FIG. 7 is a perspective view of a completed anastomosis performed with the anastomosis tool of FIG. 1, showing the topology of the anastomosis.

The graft affixer 20 may be connected to the staple holder 4 in any appropriate manner. The graft affixer 20 may be fixed to the staple holder 4, or detachable from the staple holder 4, such as disclosed in U.S. patent application Ser. No. 11/054,265. Referring to FIGS. 5-6, an example of a graft affixer 20 detachable from the staple holder 4 is shown. Referring also to FIG. 7, the detachable graft affixer 20 of FIG. 6 may also be referred to as the heel clip 20, because it may be used to provide additional sealing at the heel 22 of the anastomosis. The heel clip 20 may include a leg 28 having a free end 30. The free end 30 of the leg 28 may be substantially sharp or substantially blunt. A first tab 32 extends outward from the leg 28 of the heel clip 20. Alternately, the first tab 32 extends from a different part of the heel clip 20. Moving away from the free end 30 of the heel clip 20, a base 34 of the heel clip 20 bends or angles away from the leg 28. A second tab 36 extends outward from the base 34 of the heel clip 20. Alternately, the second tab 36 extends from a different part of the heel clip 20. Continuing along the heel clip 20 away from the free end 30 of the leg 28, a prong 38 extends from the base 34. The prong 38 may be oriented in substantially the same direction as the leg 28. Alternately, the prong 38 is oriented in a different direction from the leg 28. The prong 38 has a free end 40 that may be substantially sharp or substantially blunt. The heel clip 20 may be fabricated from a single unit of material. Alternately, at least part of the heel clip 20 is fabricated separately and connected to a remainder of the heel clip 20 in any suitable manner, such as by welding.

The heel clip 20 is detachable from the staple holder 4, and may be detachably held by the staple holder 4 in any suitable manner. As one example, the staple holder 4 includes a ledge 41 that engages the first tab 32 and a notch 42 that engages the second tab 36. The ledge 41 and the notch 42 may be configured to hold the tabs 32, 36 such that the heel clip 20 is compressed at least slightly, thereby enhancing the connection between the heel clip 20 and the staple holder 4. The staple holder 4 may include a pocket 44 or other surface or feature configured to receive at least part of the base 34 of the heel clip 20. As another example, a deflectable retainer (not shown) is connected to the staple holder 4 and is biased against the heel clip 20 and/or positioned relative to the heel clip 20 to hold the heel clip 20 in place on the staple holder 4. Alternately, the heel clip 20 may be detachably connected to the staple holder 4 in any other suitable manner. For example, the heel clip 20 may be pressure-fit to the staple holder 4. As another example, the heel clip 20 may be frangibly connected to the staple holder 4.

Figure 8:
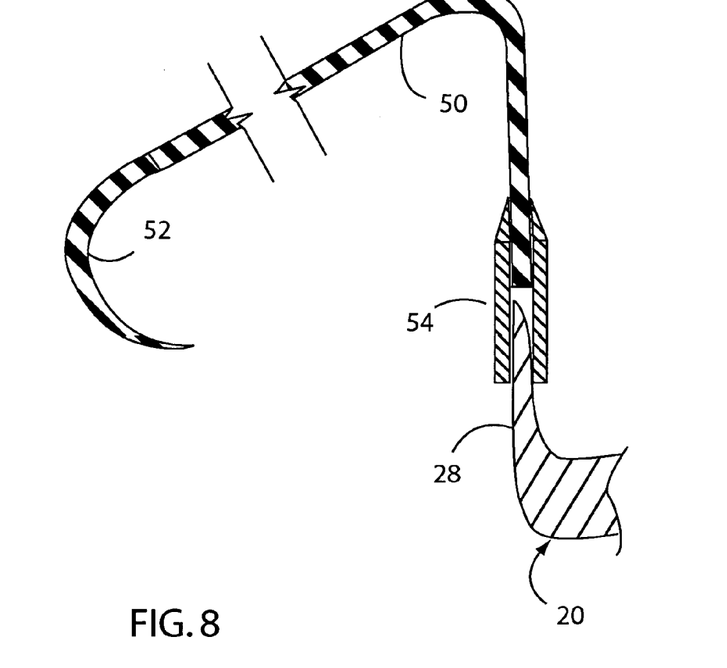
FIG. 8 is a side cross-section view of a graft affixer connected to a suture, which in turn is connected to a needle.

Referring also to FIG. 8, a length of suture 50 may be connected to the heel clip 20 to facilitate loading the graft vessel 10 onto the leg 28 of the heel clip 20. The suture 50 may be connected to the heel clip 20 detachably, or may be fixed to the heel clip 20. A needle 52 may be connected to the end of the length of suture 50 that is opposite to the end connected to the help clip 20. The needle 52 may be straight, curved, or configured in any other suitable manner. The connection between the needle 52 and the suture 30 may be made in any suitable manner; such a connection is standard in the art. The suture 50 may be any suture of suitable length, gauge and strength. The suture 50 may be composed of polypropylene, silk, wire or any other suitable material. Advantageously, the suture 50 is 7-0 or 8-0 gauge.

The suture 50 may be connected at one end to any suitable portion of the heel clip 20. As one example, the suture 50 may be connected to the leg 28 of the heel clip 20. The suture 50 may be connected to the leg 28 of the heel clip 20 such that the free end 30 of the leg 28 is located proximal to the distal end of the suture 50. However, the topology of the connection between the suture 50 and the heel clip 20 may take any suitable form.

Figure 9:
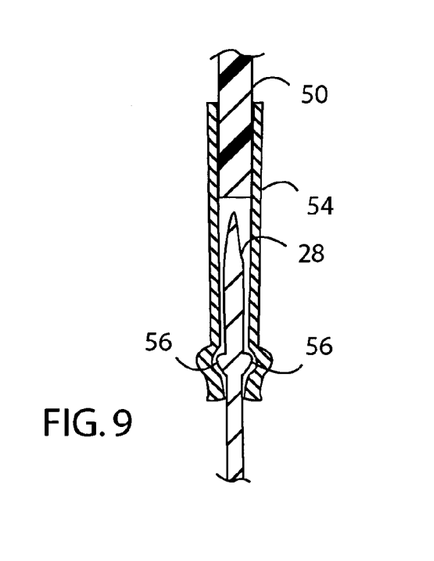
FIG. 9 is a side cross-section view of a different exemplary embodiment of a graft affixer connected to a suture, which in turn is connected to a needle.

The suture 50 may be connected to the heel clip 20 in any suitable manner. Referring to FIG. 8, as one example, a connector 54 may be used to connect the suture 50 to the heel clip 20. The connector 54 may be configured in any suitable way. As one example, the connector 54 may be a length of heat shrink tubing 54, with a lumen therethrough. In the original state of the heat shrink tubing 54, its lumen may have a diameter larger than that of the suture 50 and larger than the greatest width of the distal end of the leg 28 of the heel clip 20. One end of the heat shrink tubing 54 is placed over at least part of the leg 28, and the other end of the heat shrink tubing 54 is placed over a portion of the proximal end of the suture 50. The suture 50 and the leg 28 may touch or overlap, or may be spaced apart from one another. The heat shrink tubing 54 is then heated to a second, shrunken state, in which the heat shrink tubing 54 applies a compressive force to both the suture 50 and the leg 28 of the heel clip 20. In this way, the heat shrink tubing 54 connects the suture 50 to the heel clip 20. Referring to FIG. 9, optionally the leg 28 of the heel clip 20 may include one or more bumps 56 extending laterally therefrom. The bumps 56 facilitate the connection of the heat shrink tubing 54 to the leg 28, and further reduce any possibility of the heat shrink tubing 54 slipping off of the leg 28.

Figure 10:
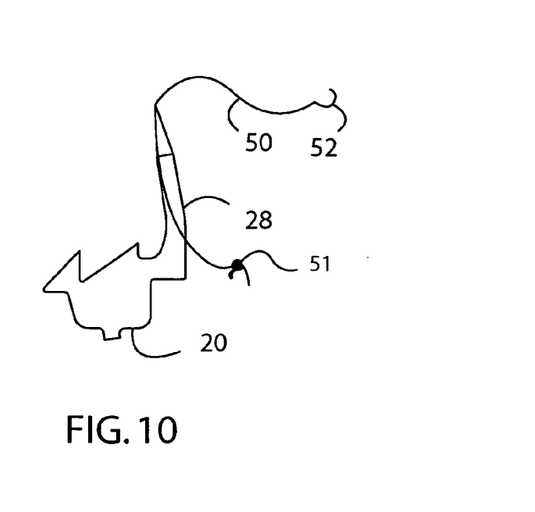
FIG. 10 is a side view of a graft affixer connected to a suture in a different manner than illustrated in FIGS. 8-9, where that suture is connected to a needle.

Referring to FIG. 10, another example of a connection between the suture 50 and the heel clip 20 is shown. A length of the suture 50 may contact and/or be connected to the heel clip 20 along part or the entire length of the leg 28. A portion of the suture 50 may be oriented substantially parallel to the leg 28. The suture 50 may be connected to the leg in any suitable manner, such as by heat shrink tubing as described above. The suture 50 may extend proximally from the leg 28 of the heel clip 20. The proximal end of the suture 50 may be knotted (for example, a single knot 51) or connected to a stop of any suitable configuration.

As another example, a portion of the suture 50 such as a length of suture 50 near one end may be compressed between the heel clip 20 and the staple holder 4. That is, a portion of the suture 50 may be trapped between the heel clip 20 and the staple holder 4. Such a fit provides enough force to ensure that the suture 50 remains trapped between the heel clip 20 and the staple holder 4 before deformation of the heel clip 20, but not so much force as to prevent the suture 50 from being released after deformation of the heel clip 20. Optionally, the suture 50 may be held to the staple holder 4 by adhesive, mechanical connection or other attachment, where the force required to detach the suture 50 from the staple holder 4 is low enough for the user to manually detach the suture 50 from the staple holder 4.

Alternately, the heel clip 20 may include an aperture (not shown) defined therein, such as through its base 34. A portion of the suture 50 extends through that aperture, and is secured to the heel clip 20 in any suitable manner, such as described above and/or below. As one example, an end of the suture 50 may be knotted, thereby preventing the suture 50 from slipping out of the aperture in the heel clip 20.

Alternately, the suture 50 may be connected to the leg 28 and/or other portion of the heel clip 20 by adhesive, by welding, by winding a portion of the suture 50 around at least a portion of the heel clip, by compression, by interference, by friction, by one or more connectors, and/or by any other suitable method and/or with any other suitable mechanism or structure.

Figure 11:
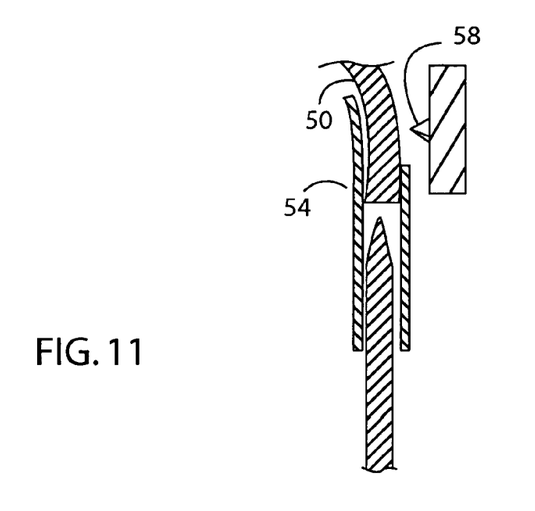
FIG. 11 is a side cross-section view of the exemplary assembly of FIG. 8 and a blade associated with the staple holder.
Figure 12:
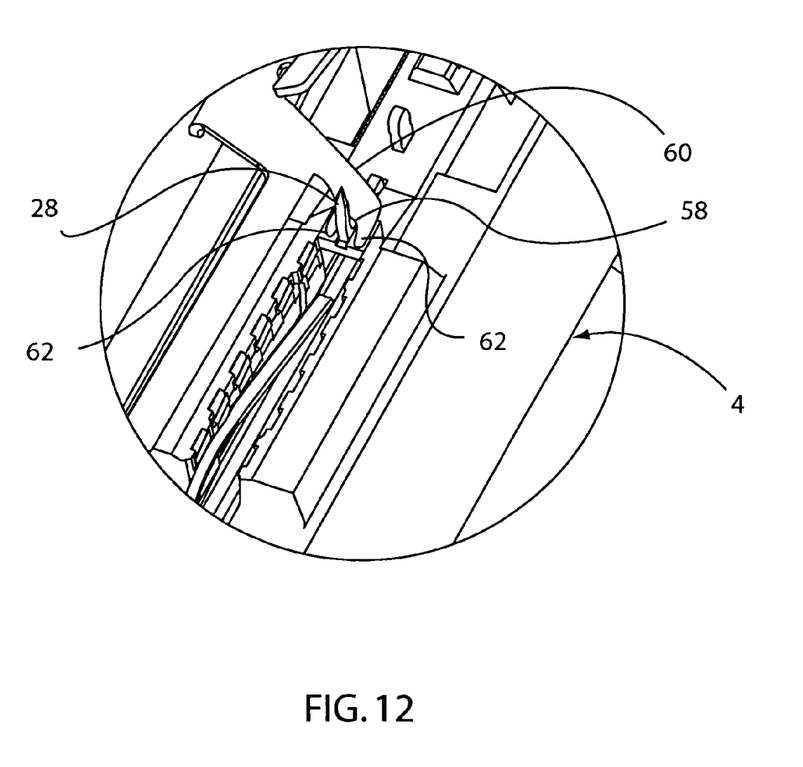
FIG. 12 is a perspective view of the exemplary assembly of FIG. 8 and a blade and arm associated with the staple holder.

Referring to FIGS. 11-12, optionally the staple holder 4 includes a blade 58 movable relative to the connection between the suture 50 and the heel clip 20. The blade 58 may be connected to one of the graft clips 18 by an arm 60. The arm 60 may be bifurcated at its free end, such that the leg 28 of the heel clip 28 can occupy at least a portion of the space between the bifurcations 62. The blade 58 may be positioned between and in proximity to the bases of the bifurcations 62. Alternately, the blade 58 may be connected to a graft clip in a different manner. Alternately, the blade 58 may be connected to a different component of the staple holder 4. For example, the blade 58 may be connected directly or indirectly to a sled movable relative to the staple holder 4, such as disclosed in U.S. patent application Ser. No. 11/054,265. Alternately, the blade 58 may be omitted altogether. Alternately, a different mechanism from the blade 58 is connected to at least one of the graft clips 18 or another portion of the staple holder, for detaching the suture 50 from the heel clip 20.

Graft Vessel Preparation

The graft vessel 10 is harvested from the patient in a conventional manner. The graft vessel 10 may be a saphenous vein, radial artery, mammary artery, or any other appropriate blood vessel. Alternately, the graft vessel 10 may be harvested from a different person or from a cadaver. Alternately, a xenograft or an artificial graft vessel may be provided. A single incision is made at an end of the graft vessel 10, and that incision extends substantially longitudinally along the graft vessel 10. The incision may be made with any appropriate surgical tool, such as a Potts scissors. When the incision is made, the graft vessel 10 may be held by hand, with a surgical clamp, or in any other suitable manner. Advantageously, the incision is substantially one centimeter long, although it may be longer or shorter if desired. Alternately, two or more flaps 12 are present at the end of the graft vessel 10. These flaps 12 may be created in any appropriate manner, such as by incising the end of the graft vessel 10 with a scalpel. However, the end of the graft vessel 10 may have more than two flaps 12.

The needle 52 is then penetrated through the wall of the graft vessel 10 slightly proximal to the proximal end of the incision. Advantageously, the needle 52 may be penetrated through the wall of the graft vessel 10 approximately one millimeter from the proximal end of the incision. This location corresponds to the heel 22 of the anastomosis to be performed and may be referred to as the heel 22 of the graft vessel 10. The needle 52 is then pulled completely through the wall of the graft vessel 10, such that the suture 50 contacts the wall of the graft vessel 10. At this time, the graft vessel 10 is registered to the staple holder 4, because the suture 50 is connected to the heel clip 20 that in turn is connected to the staple holder 4. The graft vessel 10 is then slid down the suture 50 toward the staple holder 4. This sliding motion may be referred to as "parachuting." As the graft vessel 10 approaches the staple holder 4, the graft vessel 10 is moved between the arms 8 of the staple holder 4, and the portion of the wall of the graft vessel 10 that engages the suture 50 approaches the free end 30 of the leg 28 of the heel clip 20. The graft vessel 10 then encounters the free end 30 of the leg 28, such that the leg 28 penetrates the wall of the graft vessel 10. The graft vessel 10 may be pushed down onto the leg 28 in any suitable manner, such as by hand. Optionally, a poke-through tip such as disclosed in U.S. patent application Ser. No. 11/054,265 may be utilized to push the graft vessel 10 onto the leg 28.

Next, the graft vessel 10 is angled relative to the arms 8 of the staple holder 4, as the heel of the graft vessel 10 is held substantially at a known position by the leg 28 of the heel clip 20. That is, the heel clip 20 registers the heel of the graft vessel 10 to the staple holder 4. In this way, the end of the graft vessel 10 can be prepared to a substantially constant preselected length, such as disclosed in U.S. patent application Ser. No. 11/054,265. The flap 12 is then everted onto the arms 8 of the staple holder 38. If one or more spikes 16 extend outward from at least one arm 8, the flap 12 is everted onto one or more of those spikes 16. One or more of the spikes 16 penetrate a corresponding flap 12 partially or completely, thereby assisting in holding the flap 12 in place relative to the corresponding arm 8. At least one arm 8 may include at least one graft clip 14 that exerts force on a corresponding flap 12 to hold that flap securely against the corresponding arm 8. Each graft clip 14 is movable from an open position in which the arm 4 can receive a flap 12 to a closed position in which the graft clip 14 holds the flap 12 against the corresponding arm 4. Each graft clip 14 may be rotatable, slidable, or movable in any other suitable manner between the open position and the closed position, and may be held in the closed position in any suitable manner, such as disclosed in U.S. patent application Ser. No. 11/054,265. Alternately, at least one graft clip 14 is detachable from the staple holder 4, where such a graft clip 14 is considered to be in the open position when it is disconnected from the staple holder 4 and in the closed position when it is connected to the staple holder 4.

After the graft vessel 10 is attached to the leg 28 of the heel clip 20 and the flap 12 is secured to the staple holder 4, the suture 50 may be disconnected from the heel clip 20 at any time. As one example, the suture 50 may be cut after the graft clip or clips 14 engage the flap 12 to hold it against the arms 8. A Potts scissors or other surgical tool may be used to simply cut the suture 50 at a location in proximity to the heel clip 20. Advantageously, if the suture 50 is cut, the cut is made in proximity to the heel clip 20. Alternately, the suture 50 may be cut at a later time, such as described below, or the suture 50 may be disconnected from the heel clip 20 in a different manner at this time or at a later time in the procedure.

Operation

The staple holder 4 and the anvil 6 are initially in a first position, in which at least part of the staple holder 4 is spaced apart from the anvil 6. The staple holder 4 may be rotatable relative to the anvil 6, such as by connection of the proximal end of the staple holder 4 to the proximal end of the anvil 6 by a pin, axle or other suitable structure or mechanism. The user inserts the anvil 6 into the target vessel 24, such as disclosed in U.S. patent application Ser. No. 11/054,265.

The staple holder 4 then moves to a second position closer to the anvil 6, such as by rotating relative to the anvil 6. The free end 30 of the leg 28 of the heel clip 20 is oriented in a direction generally pointed toward the anvil 6. Thus, as the staple holder 4 moves closer to the anvil 6, the free end 30 of the leg 28 penetrates through the wall of the target vessel 24. As the staple holder 4 moves closer to the anvil 6, the free end 30 of the leg 28 penetrates the wall of the target vessel 24 and contacts the anvil 6. A bending feature (not shown) may be formed in the anvil 6 such that the free end 30 of the leg 28 contacts the bending feature upon contacting the anvil 6. Additionally, or instead, the leg 28 may be curved in proximity to its free end 30. The leg 28 begins to deflect as it is pressed into contact with the anvil 6 by motion of the staple holder 4, where such deflection may be assisted by the bending feature and/or the curvature of the leg 28. As the movement of the staple holder 4 to the closed position exerts force on the heel clip 20, the heel clip 20 continues to be held by the staple holder 4 and continues to bend. This bending may occur at the junction between the base 34 and the leg 28 and/or at one or more locations along the leg 28. The junction between the base 34 and the leg 28 may be sized and/or shaped to concentrate bending at that junction, if desired.

When the staple holder 4 completes its motion to the second position, the heel clip 20 is in a closed position. The leg 28 has been bent such that its free end 30 may be oriented at least partially upward. Alternately, the free end 30 is oriented differently. Further, the free end 30 of the leg 28 may penetrate into the wall of the target vessel 24 either partially or completely when the heel clip 20 is in the closed position. In the closed position, tissue of the target vessel 24 is compressed between the leg 28 and the base 30 of the heel clip 20. Further, the heel clip 20 may engage the tissue of the target vessel 24 by penetration by the free end 40 of the prong 38, thereby providing additional security. As the heel clip 20 moves to the closed position, the first tab 32 moves inward as the leg 28 is bent. When the heel clip 20 is in the closed position, the first tab 32 has moved inward enough such that the first tab 32 no longer engages the ledge 41. In this way, the heel clip 20 is freed from the staple holder 4, such that the heel clip 20 is detached from the staple holder 4 upon its deformation to the closed position. Alternately, the heel clip 20 may be freed from the staple holder 4 in any other suitable manner.

Figure 13:
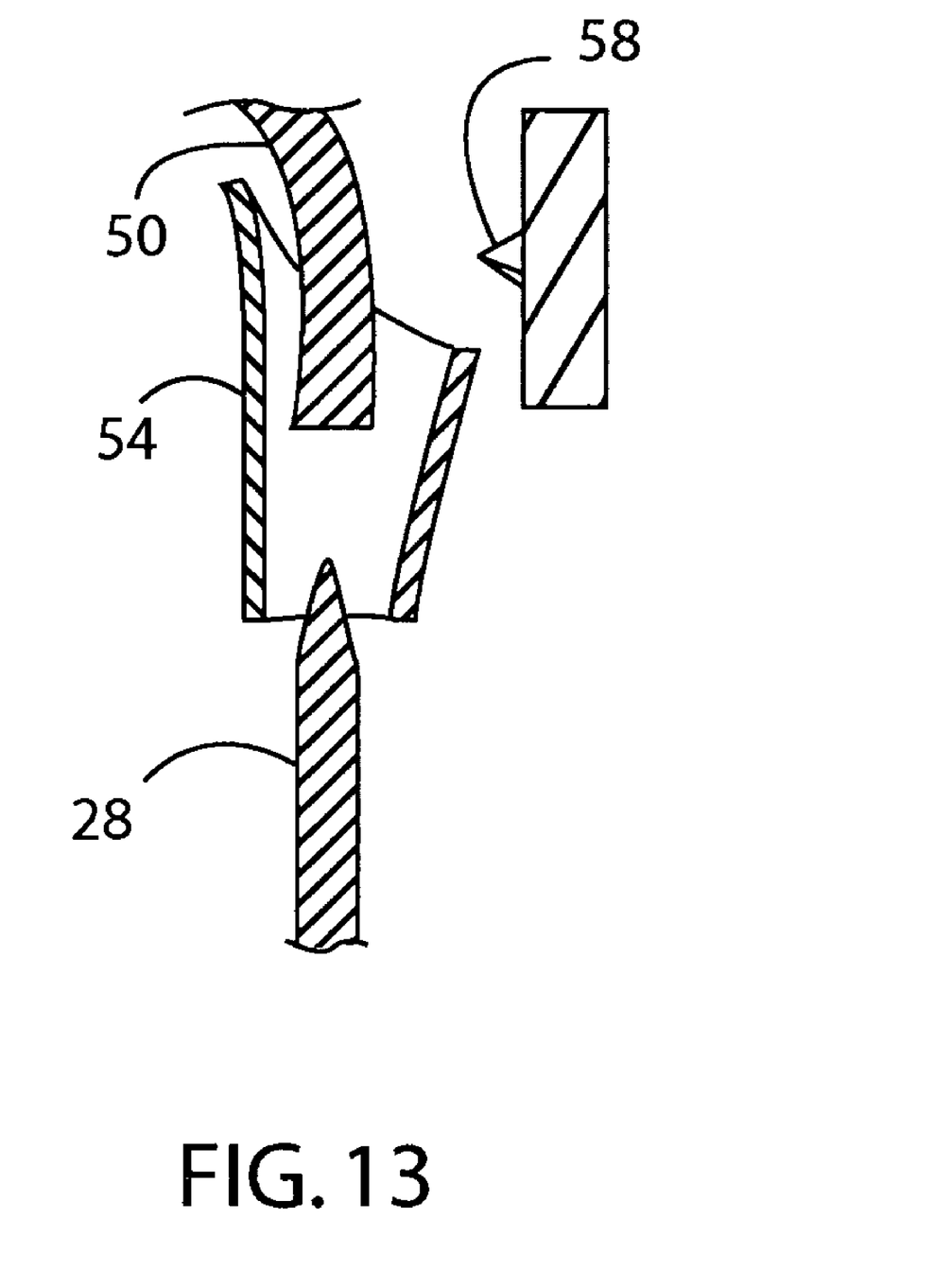
FIG. 13 is a side cross-section view of the exemplary assembly and blade of FIG. 11 and a blade associated with the staple holder after the blade has disassociated the suture from the graft affixer.

The suture 50 is then separated from the heel clip 20 in any suitable manner. As one example, the user may simply cut the suture 50 with surgical scissors or any other tool. Such a cut may be made in proximity to the heel clip 20, such that the length of suture 50 remaining in the patient is minimized. The suture 50 may be resorbable or otherwise degradable, such that the portion that remains in the patient eventually dissolves or is otherwise degraded in the body. As another example, the suture 50 may be untied from the heel clip 20. As another example, where the suture 50 is attached to the heel clip 20 by a connector 54, the connector 54 may be broken, disconnected, split, or otherwise manipulated to release the suture from the heel clip 20. Referring also to FIG. 11, the blade 56 may be moved relative to the connector 54 during closure of the heel clip 20. The blade also, or instead, may be moved relative to the connector 54 before or after closure of the heel clip 20. As the blade 56 moves relative to the connector 54, it engages and cuts the connector 54. Alternately, the blade 56 cuts the suture 50 instead of or in addition to the connector 54. Where the connector 54 is a length of heat shrink tubing 54, the blade 56 advantageously is sized and moved such that it cuts completely through the wall of the heat shrink tubing 54 along at least a portion of its length, as shown in FIG. 13. After at least part of the wall of the heat shrink tubing 54 has been cut by the blade 56, the suture 50 is released from the heat shrink tubing 54, and can be removed from the heel clip 20. The heat shrink tubing 54 itself may then be removed from the heel clip 20 such as by forceps, or may remain attached to the heel clip 20 and remain in the patient. If so, the heat shrink tubing 54 may be fabricated from material that is resorbable or otherwise degradable in the patient.

Alternately, where a portion of the suture 50 is trapped between the heel clip 20 and the staple holder 4, the suture 50 is released from engagement with the staple holder 4 after the heel clip 20 is deformed to the second position and released from the staple holder 4. That is, with the heel clip 20 no longer pressing the suture 50 into contact with the staple holder 4, the suture 50 simply falls away from the staple holder 4, such that it can be removed from the patient.

Alternately, the suture 50 may be separated from the heel clip 20 before and/or during deformation of the heel clip 20 to the second position. For example, the suture 50 may be cut by a surgical scissors or other tool prior to the deformation of the heel clip 20. As another example, the blade 58 may be moved during the deformation of the heel clip 20 such that the connector 54 is cut at least partially as the heel clip 20 is deformed. The suture 50 may be separated from the heel clip 20 in any other suitable manner.

Connectors, such as staples, are then deployed such as disclosed in U.S. patent application Ser. No. 11/054,265. Alternately, the connectors are deployed before or during deformation of the heel clip 20. An opening is created in the wall of the target vessel 24 at the anastomosis site, with an anvil knife or other suitable tool, such as disclosed in U.S. patent application Ser. No. 11/054,265. That opening may be created before, during or after deployment of the connectors. The anastomosis is then complete. The anvil 6 is then removed from the lumen of the target vessel 24 through the anvil entry hole (not shown) which may be closed in any suitable manner, such as disclosed in U.S. patent application Ser. No. 11/054,265.

While the invention has been described in detail, it will be apparent to one skilled in the art that various changes and modifications can be made and equivalents employed, without departing from the present invention. It is to be understood that the invention is not limited to the details of construction, the arrangements of components, and/or the process of performing anastomosis set forth in the above description or illustrated in the drawings. Further, the invention is not limited to the performance of anastomosis in the context of a CABG procedure. Other tissue structures than vessels may be connected together within the body utilizing the present invention. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical tool for performing anastomosis, comprising:
   a staple holder comprising two spaced-apart arms substantially fixed relative to one another, wherein each of said two spaced-apart arms holds a plurality of staples;
   a clip detachably connected to said staple holder at a location substantially proximal to said arms;
   a length of suture, wherein a portion of said length of suture is held between said clip and said staple holder; and
   a needle connected to said suture.

2. The surgical tool of claim 1, wherein said portion of said length of suture is compressed between said clip and said staple holder.

3. The surgical tool of claim 1, further comprising an anvil connected to said staple holder, wherein said staple holder is movable relative to said anvil.

4. The surgical tool of claim 1, wherein said clip is a heel clip; further comprising a plurality of staples held by said staple holder.

5. The surgical tool of claim 1, wherein said suture is not fixed to either of said clip or said staple holder.

6. The surgical tool of claim 1, further comprising a blade movable relative to said staple holder, wherein motion of the blade causes said suture to separate from said clip.

7. A surgical tool usable for preparing a graft vessel for anastomosis, comprising:
   a plastically-deformable heel clip including a base, a first leg extending at an angle from said base, and a second leg extending at an angle from said base, said second leg longer than said first leg and spaced apart from said first leg;
   a length of suture connected only to said second leg wherein a portion of said suture is detachably affixed directly and only to said second leg and not said first leg of said heel clip; and
   a needle connected to said suture.

8. The surgical tool of claim 7, wherein said second leg includes at least one bump extending therefrom.

9. The surgical tool of claim 7, wherein said suture is connected to said heel clip by a connector.

10. The surgical tool of claim 9, wherein said connector is a length of heat shrink tubing.

11. The surgical tool of claim 9, wherein said heel clip includes an aperture therethrough, wherein a portion of said suture is positioned in said aperture.

12. A method used in conjunction with the anastomosis of a graft vessel to a target vessel, each vessel including a wall encircling a lumen, comprising:
   providing a surgical stapler and a plastically-deformable heel clip including a base, a first leg extending at an angle from said base, and a second leg extending at an angle from said base, said second leg longer than said first leg and spaced apart from said first leg, detachably connected to said surgical stapler, a length of suture connected only to said second leg wherein a portion of said suture is detachably affixed directly and only to said second leg, and a needle connected to said suture;
   making at least one incision at an end of the graft vessel to create at least one flap;
   penetrating the wall of the graft vessel with said needle at a location proximal to said flap;
   parachuting the graft vessel along said suture toward said clip;
   stapling the graft vessel to the target vessel with said surgical stapler; and
   penetrating the wall of the graft vessel with at least one leg of said clip.

13. The method of claim 12, wherein said incision is substantially parallel to the longitudinal centerline of the graft vessel.

14. The method of claim 12, further comprising disassociating said suture from said clip after said stapling.

15. The method of claim 14, wherein said dissociating comprises cutting said suture.

16. The method of claim 14, further comprising a connector that connects said suture to said clip; wherein said dissociating comprises manipulating said connector to separate said suture from said clip.

17. The method of claim 16, wherein said manipulating includes cutting said connector.

18. The surgical tool of claim 1, wherein said clip is located at a lateral position substantially equidistant from the longitudinal centerline of each said arm.

* * * * *